United States Patent

John et al.

[11] Patent Number: 5,292,972
[45] Date of Patent: Mar. 8, 1994

[54] PRODUCTION OF DICHLOROHYDRIN

[75] Inventors: Christopher S. John; Wilfridus P. M. Maas, both of Amsterdam, Netherlands

[73] Assignee: Shell Oil Company, Houston, Tex.

[21] Appl. No.: 960,144

[22] Filed: Oct. 13, 1992

[30] Foreign Application Priority Data

Oct. 10, 1991 [EP] European Pat. Off. ........ 91202641.6

[51] Int. Cl.$^5$ ............................................. C07C 31/34
[52] U.S. Cl. .................................................... 568/847
[58] Field of Search ........................................ 568/847

[56] References Cited

U.S. PATENT DOCUMENTS

| | | | |
|---|---|---|---|
| 4,053,525 | 10/1977 | Saletan et al. | 260/635 E |
| 4,620,911 | 11/1986 | Blytas et al. | 204/182.4 |
| 4,657,647 | 4/1987 | Blytas et al. | 204/182.4 |
| 4,665,240 | 5/1987 | Blytas et al. | 568/847 |
| 4,900,849 | 2/1990 | Saletan | 549/521 |

FOREIGN PATENT DOCUMENTS 359331 12/1990 European Pat. Off. .

Primary Examiner—Alan Siegel

[57] ABSTRACT

The invention relates to a process for the production of dichlorohydrin which comprises reacting allylchloride, water and chlorine in a reaction zone to form an aqueous solution comprising dichlorohydrin and chlorinated organic byproducts, and contacting the aqueous solution with 1,2,3-trichloropropane to obtain an aqueous layer comprising the dichlorohydrin and an organic layer comprising the trichloropropane and chlorinated organic byproducts, separating both layers and recovering the dichlorohydrin.

7 Claims, No Drawings

PRODUCTION OF DICHLOROHYDRIN

BACKGROUND OF THE INVENTION

This invention relates to the production of dichlorohydrin. As used herein, "dichlorohydrin" refers to the isomers 1,2-dichloro-3-hydroxypropane and 1,3-dichloro-2-hydroxypropane. It is known to prepare dichlorohydrin by reacting allylchloride, water and chlorine in a dilute aqueous phase. In this process, various by-product chlorinated organic compounds can be formed as well as the desired dichlorohydrin. Also, large amounts of water are required, producing large effluent streams.

It is therefore an object of the invention to provide a process for preparing dichlorohydrin having reduced chlorinated by-products.

DESCRIPTION OF THE INVENTION

According to the invention, dichlorohydrin is prepared in a process which comprises (a) reacting allylchloride, water and chlorine in a reaction zone to form an aqueous reaction zone effluent comprising dichlorohydrin and chlorinated organic byproducts, (b) contacting the aqueous reaction zone effluent with 1,2,3-trichloropropane to obtain an aqueous layer comprising the dichlorohydrin and an organic layer comprising trichloropropane and the chlorinated organic byproducts, (c) separating the aqueous and organic layers, and (d) recovering the dichlorohydrin from the aqueous layer.

The amount of 1,2,3-trichloropropane employed is less than 10 percent by weight based on the weight of the aqueous reaction zone effluent, preferably from 1 to 8 percent, more preferably from 1.5 to 5 percent, most preferably from 2 to 4 percent. The 1,2,3-trichloropropane may be added to the reaction effluent, or 1,2,3-trichloropropane present in the reaction effluent as a reaction byproduct may be used. The 1,2,3-trichloropropane may be contacted with the aqueous dichlorohydrin solution in a cocurrent stream or in a countercurrent stream.

The preparation of dichlorohydrin may be carried out batchwise, semi-continuously or continuously. The same applies to the extraction with 1,2,3-trichloropropane.

After the aqueous effluent has been treated with 1,2,3-trichloropropane and the byproducts have been removed, the dichlorohydrin can be worked up in a manner known in the art, such as by distillation, or the aqueous dichlorohydrin solution can be directly used in the preparation of epichlorohydrin. The advantage is always that the byproducts from the dichlorohydrin preparation are no longer present and will not be found in effluent streams comprising large amounts of water.

The 1,2,3-trichloropropane containing the chlorinated organic byproducts can be passed to a distillation zone wherein 1,2,3-trichloropropane and lighter products are distilled over the top and chlorinated organic byproducts remain as the bottom products. The distilled 1,2,3-trichloropropane may be recycled to the extraction zone.

It is also possible that the extraction solvent 1,2,3-trichloropropane contains a certain amount of dichlorohydrin. This product can be distilled in the distillation zone over the top together with the 1,2,3-trichloropropane and recycled to the extraction zone. The 1,2,3-trichloropropane can be built up in the system, as it is also a byproduct of the dichlorohydrin preparation process.

Another embodiment of the invention comprises a process wherein no 1,2,3-trichloropropane is added, but directly after the reaction the reaction zone effluent is allowed to settle and a heavy organic layer comprising 1,2,3-trichloropropane (as reaction byproduct) is allowed to separate from the aqueous effluent.

EXAMPLE

An aqueous dichlorohydrin solution (1 kg), obtained from the reaction of allylchloride, water and chlorine, and 25 g 1,2,3-trichloropropane were introduced into a hydrocyclone. The hydrocyclone separated the mixture into an aqueous phase comprising the dichlorohydrin and an organic phase comprising the 1,2,3-trichloropropane.

The extraction efficiency of 1,2,3-trichloropropane was studied by analysis of hexane layers of 1:1 volume hexane extracts of the aqueous solutions of dichlorohydrin prior to and after extraction with 1,2,3-trichloropropane. Analysis of the hexane layers was carried out with a gas chromatograph equipped with a detector selected for chlorine-containing components and linear with respect to the chlorine load of these components. Chlorine components were obtained by summation of the detector response for all chlorinated components present in the hexane extracts with a higher boiling point than that of dichlorohydrin (1,2-dichloro-3-hydroxypropane, b.p. 183° C.). The extraction efficiency is the reduction of the measured chlorine content of the hexane layers obtained prior to and after treatment with 1,2,3-trichloropropane.

The extraction efficiency of 1,2,3-trichloropropane was 90%.

Example (Comparative)

The previous example was repeated except that 25 g of hexane was employed instead of 1,2,3-trichloropropane as extractant. The same analysis steps as in the previous example were carried out.

The extraction efficiency of hexane was 80%.

We claim:

1. A process for the production of dichlorohydrin which comprises:
   (a) reacting allyl chloride, water and chlorine in a reaction zone to form an aqueous solution comprising dichlorohydrin and chlorinated organic byproducts;
   (b) adding to and contacting said aqueous solution with 1,2,3-trichloropropane to obtain an aqueous layer comprising the dichlorohydrin and an organic layer comprising trichloropropane and chlorinated organic byproducts;
   (c) separating the aqueous layer from the organic layer; and
   (d) recovering dichlorohydrin from the aqueous layer.

2. The process of claim 1 in which the 1,2,3-trichloropropane is employed in an amount of less than 10 weight percent based on the weight of the aqueous solution.

3. The process of claim 2 in which from 1 to 8 percent by weight of 1,2,3-trichloropropane is employed.

4. The process of claim 1 in which the 1,2,3-trichloropropane is countercurrently contacted with the aqueous dichlorohydrin solution.

5. The process of claim 1 which further comprises passing the organic layer to a distillation zone and distilling the trichloropropane from the chlorinated organic byproducts.

6. The process of claim 5 in which the trichloropropane is recycled to the extraction zone.

7. The process of claim 1 in which step (b) comprises allowing the aqueous solution to settle so as to form a heavy organic layer comprising trichloropropane.

* * * * *